United States Patent [19]

Appelbaum

[11] Patent Number: 5,059,534
[45] Date of Patent: Oct. 22, 1991

[54] RHIZOBIUM JAPONICUM 191 NODD-RELATED GENES

[75] Inventor: Edward R. Appelbaum, Blue Bell, Pa.

[73] Assignee: Lubrizol Genetics, Inc., Wickliffe, Ohio

[21] Appl. No.: 403,907

[22] Filed: Jul. 17, 1989

Related U.S. Application Data

[63] Continuation of Ser. No. 763,934, Aug. 7, 1985, abandoned.

[51] Int. Cl.$^5$ .................. C12N 15/00; C12R 1/41; C07H 15/12
[52] U.S. Cl. ..................... 435/172.3; 435/252.2; 435/252.3; 435/320.1; 435/878; 536/27
[58] Field of Search ................. 435/172.3, 320, 320.1, 435/252.2, 252.3, 878; 536/27

[56] References Cited

FOREIGN PATENT DOCUMENTS 0130047 1/1985 European Pat. Off. .

OTHER PUBLICATIONS

Appelbaum et al. (Mar. 1986) Chemical Abstracts 104(13), Abstract No. 103230v, p. 150.
Prakash et al. (1984) J. Bacteriol. 160:785–787.
Legocki et al. (1984) Proc. Natl. Acad. Sci. U.S.A. 81:5806–5810.
Cantrell et al. (1983) Proc. Natl. Acad. Sci. 80:181–185.
Long et al. (1982) "Cloning of R. meliloti nodulation genes . . . " Nature 298: 485–488.
Downie et al. (1983) EMBO J Z:947–52, "Cloning of symbiotic region of . . . ".
Sundaresan et al. (1983) "Activation of Klebsiella . . . " PNAS 80: 4030–34.
Drummond et al. (1983) "Positive control and autogenous . . . " Nature 301: 302–307.
Simon et al. (1983) "Vector Plasmids . . . " In Molecular Genetics of Bact–Plant Interaction, Puhler, A. (ed.).
Spaink et al. (1987) Nature 328:337–340.
Egelhoff, T. T. et al. (1985), "Nucleotide Sequence of Rhizobium meliloti 1021 Nodulation Genes: nodD is Read Divergently from nod ABC",: DNA 4:241–248.
Schofield, P. R. (1984), "A Genetic and Molecular Analysis of the Nodulation Genes of Rhizobium trifolii," Doctoral thesis submitted to Australian Natl. University (Chapter Eight).
Kaluza et al. 1985, FEBS Letters 188(1):37–42.

Primary Examiner—Elizabeth C. Weimar
Assistant Examiner—David T. Fox
Attorney, Agent, or Firm—Greenlee and Associates

[57] ABSTRACT

The isolation and characterization of nodD-related genes in soybean nodulating Rhizobium japonicum is described. In R. japonicum USDA 191 two such genes have been identified, which although related in structure, have different functional properties. These nodD genes are functionally distinct from each other and from those nodD genes of other strains of Rhizobium that have been isolated and characterized to date. In particular, nodD-r1 has been found to affect nodulation on soybean and to be associated with exopolysaccharide production. In contrast, nodD-r2 affects nodulation on the tropical legume siratro. The coding sequences of both nodD genes are provided. The promoter regions of the nodD genes have also been isolated. The genes described herein, including both structural genes and their promoter regions, can be used in combination with other genetic constructs to enhance the efficiency and competitiveness of nodulation.

10 Claims, 1 Drawing Sheet

RHIZOBIUM JAPONICUM 191 NODD-RELATED GENES

This application is a continuation of application Ser. No. 763,934, filed Aug. 7, 1985, now abandoned.

BACKGROUND OF THE INVENTION

Soybean-nodulating Rhizobium species are classified as *R. japonicum*. Older literature references to *R. japonicum* refer to strains characterized as "slow-growing" Rhizobia. More recent studies of biochemical and genetic characteristics have led to reclassification of "slow-growing" Rhizobia in the genus Bradyrhizobium (Jordan, D. C. (1982) Int. J. Syst. Bacteriol. 32:136). Furthermore, certain "fast-growing" strains have been found which are classified as *R. japonicum* on the basis of their ability to nodulate Glycine Max cv. Peking, an undeveloped Asian cultivar of soybeans. One such "fast-growing" strain, USDA 191, has been found able to form fix+ (nitrogen fixing) nodules on commercial soybean cultivars, e.g., Williams (Yelton et al. (1983) J. Gen. Microbiol. 129:1537–1547). Since the literature sometimes refers to slow-growing (Bradyrhizobium) strains simply as *R. japonicum*, confusion may occur. For clarity herein, "slow-growing" commercial soybean nodulating strains, such as USDA 110 or USDA 123, are termed *Bradyrhizobium japonicum* strains, while USDA 191, a "fast-growing" strain, is termed a *Rhizobium japonicum* strain. *R. japonicum* USDA 191 is much more, amenable to genetic manipulation than *B. japonicum* strains because it grows faster, many of the primary genes for symbiosis are located on a plasmid (Appelbaum et al. (1985) J. Bact. 163:385) and transposon mutagenesis occurs at higher frequencies in *R. japonicum* than in *B. japonicum*.

The interaction between a Rhizobium strain and a leguminous plant to form a nitrogen fixing root nodule involves the participation of a number of bacterial genes which in many Rhizobium strains are located on a large plasmid known as the Sym plasmid. (For a recent review see Long, S. R. (1984) in *Plant-Microbe Interactions*, T. Kosuge and E. Nester, eds., McMillan, New York, pp. 256–306.) Analysis of USDA 191 plasmids by gel electrophoresis has revealed the presence of several plasmids including a 200 MD plasmid which hybridizes to nif and nod probes from *Klebsiella pneumoniae* and *Rhizobium meliloti* and has been designated pSym 191 (Appelbaum et al. (1985)). Genetic loci involved in nodulation, designated nod, have been cloned from the Sym plasmid DNA of several Rhizobium species (Long et al. (1982) Nature 298:485) (*R. meliloti*); Downie, J. A. et al. (1983) EMBO J. 2:947 (*R. leguminosarum*); Schofield, P. R. et al. (1983) Mol. Gen. Genet. 192:459 (*R. trifolii*); Kondorosi, E. et al. (1984) Mol. Gen. Genet. 193:445 (*R. meliloti*). A set of nod genes, designated nodA, nodB, nodC and nodD, have been identified in each case, which appear to be involved in early stages of infection and nodule development. Mutants in these genes fail to develop visible nodules and in some cases fail to display root hair curling which is believed to be an initial reaction in the nodulation process. These genes have been termed "common nod genes" because they appear to be functionally interconvertible between the species *R. meliloti*, *R. trifolii* and *R. leguminosarum*, as shown by interspecific complementation experiments of nod mutants by Sym plasmids or by cloned nod genes. The nucleotide sequence of the nodD gene of *R. meliloti* has been published by Egelhoff, T. T. et al. (1985) DNA 4:241. The sequence yields a predicted amino acid sequence of 308 amino acids which appears to be separately transcribed from nodA, B, and C in *R. meliloti*. All four genes were closely linked; however, nodD was separately transcribed in *R. meliloti*.

The function of the nodD protein has not been precisely defined. In *R. meliloti*, Tn5 insertions in nodD cause a leaky nod− phenotype; however, in *R. trifolii*, a Tn5 insertion displayed an unequivocal nod− phenotype, Schofield et al. (1983). Egelhoff et al. (1985) have suggested the possibility that nodD may be a regulatory gene.

As with any gene coding for a protein, the functional properties of the gene may vary as a result of differences in nucleotide sequence which affect the amino acid sequence of the protein for which it codes, which in turn may affect the functional properties of the protein. Such changes in gene structure may be manifested by differences in the phenotype associated with variants of the gene, differences in complementation behavior, differences in phenotypic behavior in a new genetic background as for example by transfer to a different species of host cell, or by differences in the effects produced by mutation in a gene when compared with its homolog. Such effects are well known in the art and numerous examples are documented in standard texts of molecular genetics, biochemistry or microbial genetics.

The nodulation process in soybeans differs from that in alfalfa, clover or peas in several significant respects. The soybean nodule is anatomically and metabolically different from nodules in the aforementioned legumes, being determinate as compared to the "indeterminate" nodules of the aforementioned legumes. Such differences reflect a different manner of nodule development (Newcomb, W. (1981) in Intl. Rev. Cytol. Suppl. 13 [K. Giles and A. Atherly, eds.] Academic Press N.Y., pp. 247–298). In addition, until recently only species of Bradyrhizobium were known to possess the ability to nodulate soybeans. Whether these differences in the developmental differentiation leading to complete nodule formation are solely the result of genetic differences in soybean, and whether genes of the bacteria which nodulate soybean are specialized to operate in concert with the soybean system, remain open question.

SUMMARY OF THE INVENTION

The present invention relates to the first isolation and characterization of a nodD related gene in a soybean nodulating Rhizobium strain. Surprisingly, two such genes have been found, each having different apparent functional properties as compared to the other and as compared to other nodD related sequences isolated and characterized to date. The term nodD-related gene or coding sequence is used herein to mean a gene or coding sequence having certain elements of structural similarity to the known nodD sequences but having in addition elements of structural and functional dissimilarity. The organism of origin was *Rhizobium japonicum* USDA 191.

The two genes are designated herein as nodD-r1 and nodD-r2. Both genes are useful for the genetic engineering of Rhizobium strains, including strains for inoculating soybeans. The genes can be used in combination with other genetic constructs and other promoters to enhance the efficiency and competitiveness of nodulation. In addition, nodD-r1 can be used to reduce exopolysaccharide synthesis by *R. japonicum* 191 growing in culture, thereby enhancing the ease and reducing the expense of harvesting and purifying cells under commercial culture conditions (see, e.g., Tully, R. E. (1985) Appl. Microbiol. Biotechnol. 21:252).

DETAILED DESCRIPTION OF THE INVENTION

Figure 1:
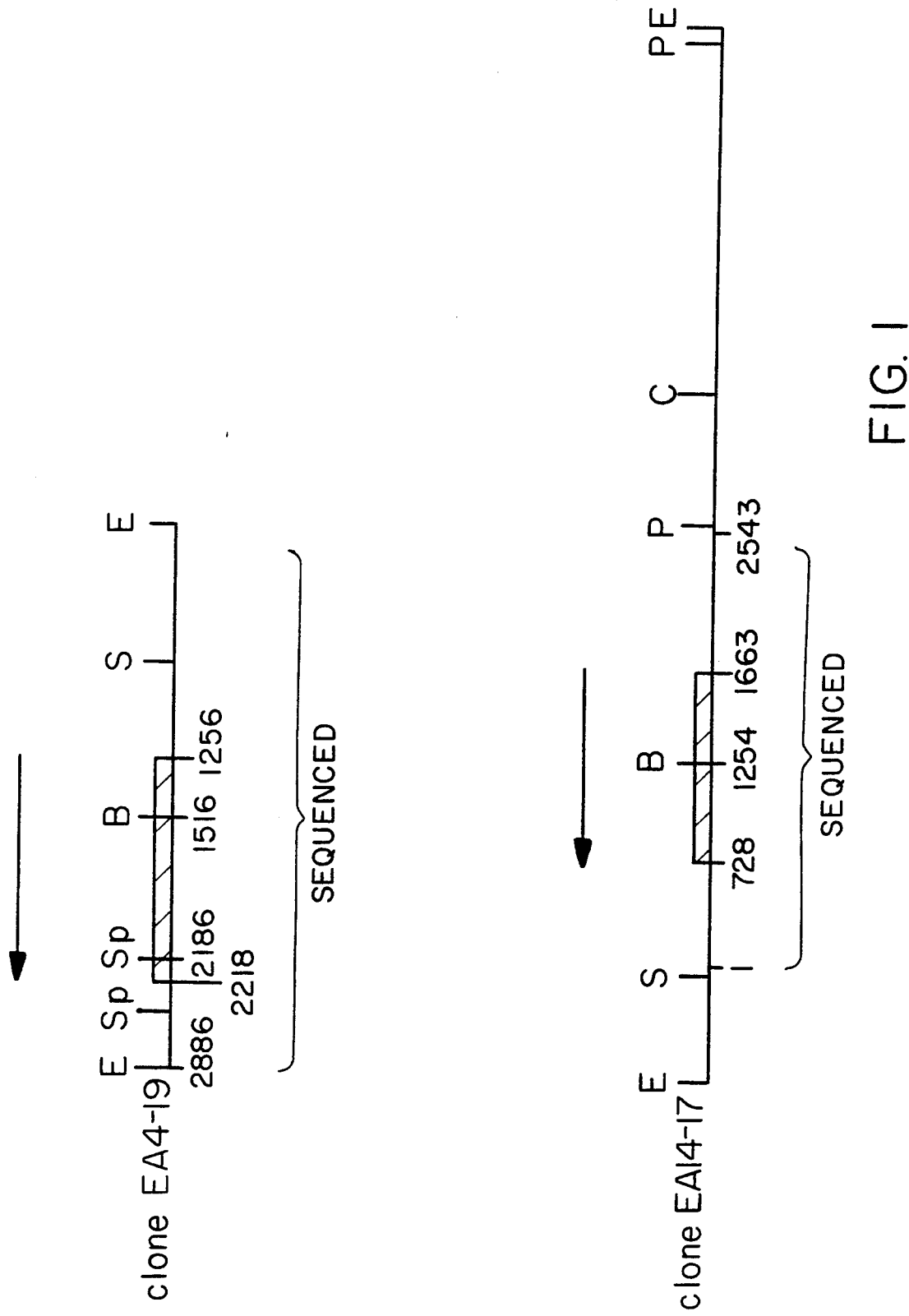

The nodD-related genes of USDA 191 were isolated by probing an EcoRI digest of genomic DNA from USDA 191 by hybridization to pRMSL42, which contains all of nodA, nodB and portions of nodD and nodC of *R. meliloti* (Egelhoff (1985)). Two strongly hybridizing fragments were found, one of approximately 6 kbp and another of about 3 kbp designated EA14-17 and EA4-19, respectively. Fragment EA14-17 contained nodD-r1 and fragment EA4-19 contained nodD-r2. Neither the 6 kbp nor the 3 kbp fragments contained sequences homologous to nodA, nodB or nodC. Sequences related to nodB and/or nodB and to nodC were identified on a separate EcoRI fragment of 9.6 kbp. Therefore, the genetic organization of the nod genes in USDA 191 differs from that of previously reported strains in that the nodD related sequences are separated from the nodA, nodB, nodC locus by at least several kilobases, as well as being separated from each other.

FIG. 1 shows partial restriction maps of the two EcoRI fragments. Substantial portions of each have been sequenced, including all of the nodD-related coding regions. In the 3 kb EcoRI fragment, 2886 base pairs have been sequenced corresponding to virtually the entire fragment. The hatched regions shows diagrammatically the position of the nodD-r2 open reading frame which codes for a protein of 321 amino acids having a molecular weight of 36,393. The arrow shows the direction of transcription of nodD-r2 with respect to the restriction map of the 3 kb fragment. In the 6 kb fragment, a sequence of 2543 base pairs has been determined, spanning the open reading frame and coding region of EA14-17, which codes for a protein of 312 amino acids having a molecular weight of 35,300. The arrow indicates the direction of transcription with respect to the restriction map. In FIG. 1, the positions of restriction enzyme cleavage sites are labelled as follows: E=EcoRI, B=BamHI, S=SalI, P=PstI, Sp=SphI and C=ClaI. Table 1 sets forth the DNA sequence of nodD-r2 including the coding sequence and 356 bases of 5' untranslated sequence containing the promoter and 82 bases of 3' untranslated sequence. Table 2 contains the nucleotide sequence of nodD-r1 including the coding sequence, 337 base pairs of 5' untranslated sequence containing the promoter and 128 base pairs of 3' untranslated region. Table 3 shows the amino acid sequences coded by nodD-r2 and nodD-r1, respectively. The predicted amino acid sequences of nodD-r2 and nodD-r1 showed about 70% homology and each of these was about 70% homologous to amino acid sequences predicted from the sequence of the nodD gene of *R. meliloti*. Given the functional differences described infra, it is apparent that the degree of non-homology is sufficient to create significant functional dissimilarities.

The functional attributes of the nodD-related genes of USDA 191 are summarized as follows: Mutants in nodD-r1 are unable to form soybean nodules rapidly and efficiently; soybean nodulation is delayed and those nodules which are formed have a reduced ability to fix nitrogen, about one-fourth that of normal mature nodules. Constructs of USDA 191 containing extra copies of nodD-r1 carried on vector pRK290 form substantially less exopolysaccharide than wild-type USDA 191 on several different laboratory media. NodD-r1 is expressed in free-living cells. NodD-r1 on a broad-host range plasmid cannot restore the ability to nodulate clover to an *R. trifolii* nodD⁻ mutant which is otherwise unable to nodulate clover.

Mutants of the USDA 191 nodD-r2 are unable to nodulate the tropical legume siratro in contrast to the wild-type and to mutants of nodD-r1. Constructs of USDA 191 containing extra copies of nodD-r2 carried on vector pRK290 produce no observable change in exopolysaccharide production, as judged by colony morphology. In contrast to nodD-r1, nodD-r2 on a broad host range plasmid is able to complement a *R. trifolii* nodD⁻ mutant when transferred thereto, restoring the ability to nodulate clover.

The transfer of both USDA 191 nodD-related genes to *R. meliloti* or *R. leguminosarum* (along with other genes contained in the USDA 191 Sym plasmid) does not result in normal soybean nodule formation by such strains. Instead, aberrant nodules are formed which lack nitrogenase activity, do not contain leghemoglobin, nodulin 35 or nodulin 29, and it is not possible to recover viable bacteria from such aberrant nodules. The *R. meliloti* recipient was a wild-type strain with respect to its own symbiotic genes whereas the *R. leguminosarum* strain contained a deletion of its own symbiotic genes. In contrast, mobilization of the USDA 191 Sym plasmid containing both nodD-related genes to ANU265, a pSym-cured derivative of the broad host range, fast-growing strain NGR234, enabled the ANU265/pSym191 transconjugants to form normal nitrogen-fixing nodules on soybeans.

A comparison of the two USDA 191 nodD-related gene-coded amino acid sequences with the amino acid sequences in a protein sequence data base has revealed an unexpected homology between these genes and the lysR gene of *E. coli*. The lysR function is that of a regulator of transcription of a gene in the biosynthetic pathway for the amino acid lysine. In addition, lysR provides a feedback regulation on its own expression. (Stragier, P. et al. (1983) J. Mol. Biol. 168:333.) Moreover, since lysR regulates lysA in response to diamino pimellic acid, which is a bacterial cell wall component, the nodD-related genes may likewise mediate the expression of other nod genes in response to cell wall components or to other substances released by either the Rhizobium or the soybean during the Rhizobium-soybean interaction. While the foregoing observations suggest a regulatory function for the nodD-related genes of USDA 191, the present invention does not depend on a theory of nodD-related gene function for its successful operation.

The cloned USDA 191 nodD-related genes nodD-r1 and nodD-r2 are useful for genetic manipulation of USDA 191 and other soybean nodulating bacteria to modify such parameters as the rate, efficiency, competitiveness and cultivar specificity of soybean nodulation. In addition, nodD-r1 is useful for modulating exopolysaccharide production by Rhizobium strains grown in culture, the latter property being significant because exopolysaccharide synthesis limits the productivity of commercial Rhizobium production methods and interferes with separation techniques for concentration and purification of cells from the culture medium. A variety of genetic manipulations known in the art may be used to affect gene dosage, rate and timing of gene expression, or modulation of gene expression by environmental variables. These techniques include but are not limited to expressing one or both of the genes under control of other promoters, modifying the gene dosage in the host cell, providing for inducible or constitutive expression of one or more gene copies and by the construction of translational fusions which combine the functions of the nodD-related genes with one another or with other genes. Other techniques of genetic manipulation affecting the rate and timing of expression and the conditions under which up regulation and down regulation occur may be employed, as will be understood by those of ordinary skill in the art. The nucleotide sequence data disclosed herein provide the means for making the described gene constructs using known techniques of DNA sequence modification, including, for example and without limitation, the use of restriction endonucleases, ligases, exonucleases, and processes of site-directed mutagenesis and chemical DNA synthesis.

The promoters of nodD-r1 and nodD-r2 are useful for the expression of coding sequences other than the nodD-r1 and nodD-r2 structural genes normally associated therewith. Such coding sequences (termed extraneous coding sequences herein) may be derived from other genes of the same or different organisms, or from synthesized DNA or from a combination of sources forming chimeric coding sequences, the structural limitations being only those well known in the art for translatable coding sequences. The formation of a composite gene comprising an extraneous coding sequence and a promoter of nodD-r1 or nodD-r2 leads to expression of the composite gene under the circumstances characteristic for nodD-r1 or nodD-r2 expression. For example, the nodD-r1 promoter drives expression both in the free-living bacteria and in soybean nodules; the nodD-r2 promoter drives expression in soybean nodules and may also be expressed in the free-living Rhizobia.

A promoter is defined herein as the nucleotide sequence upstream from the transcriptional start site containing all the regulatory regions required for transcription. The promoter region may be partly defined by the technique of S1 nuclease mapping, which identifies the transcription start site. Further definition of the promoter is based on function. Parts of the sequence proximal to the transcription start site are often essential for promoter function while more distal upstream segments may function to provide "fine tuning" response to controlling substances. Certain consensus sequences have been shown to be characteristic of procaryotic promoters (Rosenberg and Court (1979)). The foregoing criteria can be used to identify the nodD-r1 and nodD-r2 promoters of R. japonicum USDA 191 with reasonable certainty within the 5' untranslated region upstream from the start of the nodD-r1 or nodD-r2 coding region. The nodD-r1 promoter is located in the sequence extending from about position 1970 (Table 2) to the transcription start site (a point upstream from the translation start at position 1663). The nodD-r2 promoter is located in the sequence extending from about position 951 (Table 1) to the transcription start site.

The sequence data provided herein, combined with methods known in the art, are sufficient to enable those of ordinary skill to construct desired composite genes whose expression is controlled by nodD-r1 or nodD-r2. Such methods include, but are not limited to, restriction endonuclease cutting at desired points in the sequence, ligation of desired fragments to other desired DNA fragments, chemical synthesis of oligonucleotides and site-directed mutagenesis.

Sequence variants of promoters and coding sequences are known to be feasible without substantially affecting function. Some such variants, known as allelic variants, occur with limited frequency in nature. For coding sequences, homologs with different nucleotide sequences coding for the same amino acid sequence are known to be possible from the nature of the genetic code. Other variants which affect the amino acid sequence are possible which nevertheless have substantially unaltered functional properties. For promoters, certain parts of the sequence may be essential while variation may be permissible in other parts without affecting the qualitative and quantitative functional properties of the promoter. Based on comparisons of promoters with similar functions, variations that do not substantially affect promoter function are acceptable and remain distinctive provided overall homology is 90% or greater. Therefore, the scope of interchangeable equivalents includes homologs coding for a functionally equivalent protein, in the case of coding sequences, and functionally equivalent homologs having at least 90% sequence homology in the case of promoters.

The following examples further illustrate the invention. Except as noted hereafter, standard techniques for cloning, DNA isolation, amplification and purification, for enzymatic reactions involving DNA ligase, DNA polymerase, restriction endonucleases and the like, and various separation techniques are those known and commonly employed by those skilled in the art. (See, for example, R. Wu, ed. (1979) Meth. Enzymol. 68; R. Wu et al., eds. (1983) Meth. Enzymol. 100, 101; L. Grossman and K. Moldave, eds. (1980) Meth. Enzymol. 65; J. H. Miller (1972) *Experiments in Molecular Genetics*; R. Davis et al. (1980) *Advanced Bacterial Genetics*; R. F. Schleif and P. C. Wensink (1982) *Practical Methods in Molecular Biology*; and T. Maniatis et al. (1982) *Molecular Cloning*.) Abbreviations, where employed, are those deemed standard in the field and commonly used in professional journals of wide circulation such as those cited herein. The term "cloned" used in regard to DNA sequences means specific DNA sequence isolated and purified essentially free of contaminating DNA, except that cloned DNA may be carried as part of a vector or other replicatable entity, from which the cloned DNA may be separated by conventional techniques including restriction enzyme digestion and electrophoresis.

EXAMPLE 1

Isolation and Characterization of nodD-r1 and nodD-r2

Total genomic DNA of USDA 191 was digested with EcoRI and fractionated by agarose gel electrophoresis. The plasmid pRMSL42, obtained from S. L. Long, was used as a hybridization probe, under conditions of Southern hybridization, to identify sequences homologous to those on the probe, which contains all of R. meliloti nodA and nodB, as well as portions of nodD and nodC. Three strongly hybridizing EcoRI fragments of 9.6 kb, 6.0 kb and 3.0 kb, respectively, were present in USDA 191 but absent from derivatives lacking the USDA 191 Sym plasmid. The 9.6 kb fragment was found to contain sequences homologous to nodC and to nodA and/or nodB but lacked nodD homology. However, both the 3.0 kb and the 6.0 kb fragments contained regions of homology to the R. meliloti nodD region.

A cosmid clone bank was prepared by packaging partially EcoRI-digested genomic USDA 191 DNA with the vector pSUP205 (Simon, R. et al. (1983) Bio-technology 1:784). Screening of this bank with the nod-specific fragment of pRMSL42 revealed several clones containing USDA 191 nod-related genes. A cosmid containing the 3.0 kb fragment and flanking fragments did not contain the 6.0 kb or 9.6 kb fragments. A cosmid containing the 6.0 kb fragment and flanking fragments did not contain the 3.0 kb or 9.6 kb regions. Therefore, the nodD-related sequences in these two locations were separated from each other and from the nodA, nodB, nodC locus by at least several kilobases. No nodD-related sequences located adjacent to nodA, nodB and nodC were detected.

Further hybridization experiments showed that the nodD region of R. meliloti hybridizes only to the central portions of the 3.0 kb and 6.0 kb fragments of USDA 191. The two USDA 191 fragments also hybridized to each other, but only the central portions were homologous. The central hybridizing regions were sequenced using the technique of Maxam, A. and Gilbert, W. (1977) Proc. Natl. Acad. Sci. 74:560. The nodD-related sequence associated with the 3.0 kb fragment was designated nodD-r2; that associated with the 6.0 kb fragment was designated nodD-r1. 2886 base pairs of the 3.0 kb fragment were sequenced and 2543 base pairs of the central, nodD-related portion of the 6.0 kb fragment were sequenced. The sequences revealed in each case major open reading frames of approximately 936 base pairs length for nodD-r1 and 963 base pairs for nodD-r2. The sequences of EA14-17 and EA4-19 including the open reading frames and portions of 5' and 3' untranslated regions are shown in Tables 1 and 2. The 300 base pair regions preceding (5' to) the open reading frames contain several regions of homology with the regions preceding nodD in R. meliloti and these regions are identified as the promoters of the two nodD-related genes of USDA 191.

EXAMPLE 2

Mutation and Complementation Analysis of nodD-related Genes

Derivatives of USDA 191 were constructed containing mutations in each of the nodD-related genes. Insertion mutations were generated by making an insertion of a kanamycin-resistance gene at unique BamHI sites located within the open reading frames of each nodD-related gene. The BamHI site of nodD-r1 is located at the nucleotide sequence coding for amino acid 135 and the BamHI site of nodD-r2 is located at the nucleotide sequence coding for amino acid 88. The locations of the BamHI sites are shown schematically in FIG. 1. The inserted kanamycin-resistance gene was flanked by sequences containing BamHI sites. In the case of nodD-r1, a second mutation was generated by deleting 1.9 kilobases of DNA lying between the ClaI site upstream from the BamHI site and replacing the deleted segment with the kanamycin-resistance gene. The mutations on the clones were each crossed back into wild-type USDA 191 by double homologous recombination, selected by resistance to kanamycin. The structures of the insertion and deletion mutations in the mutated USDA 191 genome were confirmed by blot hybridization analysis.

The insertion mutation and deletion mutation in nodD-r1 caused a leaky fix− phenotype on cultivars Williams and Peking. Four-week old plants were faintly green in color, intermediate between the green of normal fix+ inoculated plants and the yellow of uninoculated plants. Acetylene reduction activity, a measure of the nitrogenase activity, was about one-fourth of wild-type levels. Nodule numbers were about one-half of wild-type levels. A time course study showed that nodules and nitrogenase activity appeared somewhat more slowly in the mutant than in the wild-type. Thus nodule development appeared to be delayed by one or two days in nodD-r1 mutants and the nodules did not fully develop even after 4–6 weeks. In a competitive inoculation, short delays in the application of one strain will lead to a severe underrepresentation of that strain in the nodules which subsequently form. The delayed nodulation mutants of nodD-r1 behave in an analogous manner even when presented simultaneously in a mixture of wild-type and mutant bacteria. In these experiments, stationary phase cultures of each strain were mixed to give a 10:1 ratio of mutant to wild-type viable cells and inoculated on soybean cultivar Peking. The plants were grown in vermiculite in Leonard jars. After 4 weeks, nodules were harvested from the root surfaces, surface sterilized and crushed, then plated on differentially selective medium. Mutant bacteria were found in only 12.5% of the nodules and all such nodules were also inhabited by wild-type cells.

The 6.0 kb fragment containing nodD-r1 was cloned into the broad host range vector pRK290, then transformed back into USDA 191. Colonies containing the extra copies of the nodD-related gene showed altered morphology, being smaller and much less gummy in appearance than wild-type USDA 191. The effect was apparent on several different laboratory media, including yeast-mannitol agar, tryptone-yeast extract (Bergerson, F. J. (ed.) (1980) Methods for Evaluating Biological Nitrogen Fixation, J. Wiley, New York) and minimal medium with glycerol as carbon source and monosodium glutamate as nitrogen source (Bishop, et al. (1976) Plant Physiol. 57:542). The change in colony morphology was not observed in control strains of USDA 191 containing the vector pRK290 alone or with clones containing the insertion mutation in nodD-r1 described previously. The change in colony morphology was seen regardless of the orientation of the 6.0 kb fragment in pRK290. These results support the conclusion that the effect on colony morphology was due to the presence of the nodD-related gene and that the gene was being expressed from its own promoter. The result further demonstrates that nodD-r1 is expressed in free-living cells. The altered appearance of the colonies is interpreted as a reduction in exopolysaccharide synthesis.

The effects of mutation in the nodD-r2 were more subtle than those of mutation in nodD-r1. Most significantly, mutants in nodD-r2 were defective in the ability to nodulate siratro, a tropical legume. Extra copies of the unmutated nodD-r2 produced no observable effect on nodulation or colony morphology. Unlike the 6.0 kb fragment containing nodD-r1, the 3.0 kb fragment containing non-mutated nodD-r2 was able to complement (restore nodulation ability to) a nodD− mutant of R. trifolii. Therefore, although R. trifolii nodulation ability is restored by nodD-r2, R. trifolii is unable to nodulate siratro, whereas the ability to nodulate siratro is associated with the function of one of the nodD-related genes of USDA 191, specifically nodD-r2. The result does not rule out the possibility that other genes may play a part in these phenomena, but it does indicate that EA4-19 functions differently from the nodD gene of *R. trifolii*. Complementation of the *R. trifolii* nodD⁻ mutant was not observed with the 6.0 kb clone containing nodD-r1.

GENERAL CONCLUDING REMARKS

In accordance with the foregoing disclosure, clones of DNA coding for nodD-related genes of USDA 191 having unique and distinctive functional attributes are provided, useful for the modification of soybean nodulating bacteria to improve the timing, efficiency and competitiveness of the bacteria in the nodulation process. As is well known in the art, modifications of coding sequences can be made without modifying the underlying function of the protein coded thereby. Such modifications may or may not be associated with change of functional attributes. Such modifications would not effect amino acid sequence, efficiency of translation or transcription and such modifications would not affect the functional attributes of the genes as herein defined and disclosed, are deemed to be mere trivial variance or equivalence, within the scope of modifications obvious to those of ordinary skill in the art and within the scope of the appended claims.

The following have been placed on deposit with the Agricultural Research Culture Collection (NRRL), Peoria, Ill., on July 29, 1985:

*E. coli* carrying clone EA4-19; NRRL B-15985
*E. coli* carrying clone EA14-17; NRRL B-15986

TABLE 1

Sequence of nodD-r2

| | | | | | | |
|---|---|---|---|---|---|---|
| 901 | TTTTTACCGA | CAGATCAGCT | TTGCGCTTGA | AGCGCCGCTT | GCCGTCCCGT | CTGGCGGCGG |
| | GCCCGCGAGG | AACGGCGAAA | AGGCGGCGCC | GAAGCCCCTG | CATTGTTAGT | GGCAAGGCTG |
| | TTGCGGTGGG | CGTTGACGGT | TTCGCTCCGG | CTCGACCCTA | CGGTCGAAAA | GACGAAATGG |
| | CAGGAGCGGT | CGGCCGTCTT | GCCACAAAGC | CTGATCTTCA | GGAGGCGCAT | GTAAGAGGGC |
| | GGGCGACGGC | ATGAGCCGTG | AATGCACTTG | ACTTCAGATT | AATTAAGCGC | TTTCTAACGA |
| | TTTGCATAAT | TGATCGTTCG | GATGACAACC | ATCCGCACTG | TGGATTCGCC | AGAAC ATG CG |
| | TTTTAAGGGC | CTTGATCTCA | ATCTCCTCGT | TGCGCTCGAC | GCACTGATGA | CCGAACGCAA |
| | ACTCACGGCC | GCTGCACGCA | GCATCAACCT | GAGCCAGCCG | GCGATGAGCG | CAGCCATCAC |
| | CCGGCTTCGG | ACCTATTTCC | GCGACGAGCT | ATTTACCATG | AATGGTCGCG | AACTTGTACC |
| | AACTCCGCGA | GCAGAAGCGC | TCGCACCCGC | AGTCCGCGAA | GCCCTGCTGC | ACATCCATCT |
| | CTCCATCATT | TCATGGGATC | CGTTCAACCC | AGCGCAGTCA | GATCGCAGTT | TCAGGATCAT |
| | TCTTTCCGAC | TTCATGACGC | TAATGTTTTT | CGAAAGGGTT | GTGGTGAGAG | TGGCGCGGGA |
| | AGCGCCCGCC | GTCAGTTTCG | AGTTGCTGCC | GTTTTCCGAT | GAGCCAGATG | AGCTTCTCCG |
| | GCGTGGTGAT | GTCGATTTCC | TGATCCTACC | AGAAATGTTC | ATGTCGCACA | CGCATCCCAG |
| | AGCGAAGCTG | TTCGATGAGA | GATTCGTGTG | CGTGAGTTGC | CCAACGAACC | AGAAGCTACC |
| | GCCGCAGCTC | TCCATCGACA | ACTATGTATC | AATGGGGCAT | GTTGCGGCCC | AATTCGGGAA |
| | GCAGCGGCCT | TCCGTGGAGG | AATGGCTATT | GCGCGAGCAC | GGACTGCGAA | GACGGGTCGA |
| | AGTCGCCGTG | CCGGGTTTTA | CCATGATCCC | GCCTTTTTTG | TCGGGCACTG | ACCGCATAGC |
| | GACCCTCCCG | TTACGACTGG | CGATGCACTT | CGCAAAAGCC | ATTCCCCTGC | GGATCACCGA |
| | ACTTCCGCAA | CCCATTTTTC | CCGCGTTCAC | CGAGGCTGTC | CAGTGGCCCG | CGCCTCACAG |
| | CAGTGATCCG | GCCAGTCTCT | GGATGCGCGA | GATATTTCTA | CAGGAGGCGT | CTCGCGTTGA |
| | ATTTCAATCC | GAAACTTCGG | CGCATGCTCT | ATCATCATCT | CAATTGCCTA | CATGCCTC_T_A |
| | _A_AGCCGACGG | CGCAACTCGC | CACCCTTGAG | CCCGCAACTG | CACGGTCGGC | TCAGGGTCGA |
| | GCAGTTTGGC | TGCGGGTTGC | 2300 | | | |

TABLE 2

Sequence of nodD-r1

| | | | | | | |
|---|---|---|---|---|---|---|
| 2000 | GAAGAACAGG | CTAACCAAGC | CGGAGGATCA | CTCCCTTATC | GGGGATCAGG | TGGTCACCGA |
| | CGTCAGCTCT | CGAAAGTGCC | GGGGTCCGGG | TTGCACACCT | TTCTCATCAG | CACGCTGGAG |
| | AGGCCTCTGC | AAGCCGAAGT | TTTGTCCAAC | GCACCACTCA | TTTGGTGTGT | CGAATGTGGT |
| | GGGATAGTCC | CACGCTCTTT | ACGGTACTCG | GGACGGAGTG | CGCTCCACTC | CCTCATGCTC |
| | TTCTGAGCAG | CGGGAACAAG | GCAACGGCGC | TCACTCTGTA | ACATCACTGA | AAACTACCTG |
| | TTCTATGAGG | GTAGAAACGC | TTTGGTTGAA | TTAAATA ATG | CG TTTTAAGG | GACTTGATCT |
| | TAATCTGCTC | GTAGCGCTCG | ATGCTCTGAT | GACAAAGCGA | AGCGTTACCG | CAGCTGCTCG |
| | CAGTATCAAC | CTCAGTCAGC | CGGCCATGAG | CGCCGCCATC | GCCCGCCTAC | GCACCTATTT |
| | CGGCGACGAC | TTGTTCACGA | TGCGAGGTCG | CGAACTTATC | CCAACTCCGC | GTGCGATAGC |
| | GCTCGCCCCC | GCAGTCCGCG | ATGCTCTGCT | GCACATCCAG | TTCTCCATCA | TTTCTTGGGA |
| | TATGTTTAAC | CCAGTTCAGT | CGCAGCGACG | CTTCAGGATC | AGGCTTTCCG | ACGTCATAAT |
| | GCTGGTGTTT | TTTGAAAGAG | TCGTGAAGCG | GCTGGCGCGA | GAGGCGCCTG | GCATCGGCTT |
| | CGAGTTGCTG | CCTCTCACTG | AGGATCCCGA | TGAACTTCTC | CGGTACGGTG | ACGTCGATTT |
| | CGTGATCCTT | CCGGAATTGT | TCGCGTCGAG | CGATCATCCA | AAGGCGAAAC | TGCTCGACGA |
| | CACGCTGGTT | TGCGTAGGTT | GCCCCACTAA | CAAGCAGTTA | AAACGGCAGC | TTTCTTTCGA |
| | AAACTACGGA | TCGATGGGTC | ATATTGCGGC | TAAGTTCGGA | CGTACGCTAA | AGCCCTCCAT |
| | CGAGAATTGG | TTGTTGCTTG | AGCACGGTCT | CAAGAGGCGC | ATCGAAGTCG | TCGTGCCGGG |
| | ATTTAGTCTA | ATCCCGCCTT | TGCTGTCGGG | AACCGATCGC | ATAGCGACCA | TGCCGTTACG |
| | GCTGGTGGAA | CATTTCGCAA | AAACAACGCC | GCTGCGGGTC | GCCGAACTTC | CACTGGCACT |
| | TCCACCATTC | GCCCAAGCTG | TCCAGTGGCC | TAGCCTACAC | AACAGGGATC | AGGCGAGCAT |
| | CTGGATGCGG | CAGGTACTAC | TACAGGAAGC | GTTGCACATG | ACAACTCCGC | GTGATTCAGT |
| | GGAATATCGA | CCC_T_AGTCGT | TCGCAGCCGC | GGATTTGACC | GGCTTTGAGA | CACCCTGCTC |
| | ACGATCAATG | TGCCGCCCCG | CCATGATCAT | GAAGCAAGAC | CCTGGTACAC | GGCTTCGGCC |
| | GCGGAGTGGG | CTTTTGTGTG | 601 | | | |

TABLE 3a

| AMINO ACID ABBREVIATIONS | |
|---|---|
| A = Ala = Alanine | M = Met = Methionine |

TABLE 3a-continued

AMINO ACID ABBREVIATIONS

| | |
|---|---|
| C = Cys = Cysteine | N = Asn = Asparagine |
| D = Asp = Aspartic Acid | P = Pro = Proline |
| E = Glu = Glutamic Acid | Q = Gln = Glutamine |
| F = Phe = Phenylalamine | R = Arg = Arginine |
| G = Gly = Glycine | S = Ser = Serine |
| H = His = Histidine | T = Thr = Threonine |
| I = Ile = Isoleucine | V = Val = Valine |
| K = Lys = Lysine | W = Try = Tryptophan |
| L = Leu = Leucine | Y = Tyr = Tryosine |

What is claimed is:

1. A cloned DNA molecule comprising a nodD-related gene of *Rhizobium japonicum* USDA 191 selected from the group consisting of nodD-r1, nodD-r2, and allelic variants thereof having unaltered functional properties.

2. The DNA of claim 1 wherein the DNA molecule is contained in a plasmid.

3. The DNA of claim 1 wherein the DNA molecule is contained in a plasmid capable of multi-copy replication in a Rhizobium host.

4. The DNA molecule of claim 1 wherein said gene is nodD-r1.

5. The DNA molecule of claim 1 wherein said gene is nodD-r2.

6. A promoter selected from the group consisting of promoters of nodD-r1 and nodD-r2 of *Rhizobium japonicum* USDA 191, in combination with an extraneous coding sequence, the combination being expressible in a Rhizobium host.

7. The promoter of claim 6 included within a plasmid.

8. The promoter of claim 6 included within a plasmid capable of multi-copy replication in a Rhizobium host.

9. The promoter of claim 6 of nodD-r1.

10. The promoter of claim 6 of nodD-r2.

* * * * *